United States Patent

Suzuki et al.

[11] Patent Number: 5,283,064
[45] Date of Patent: Feb. 1, 1994

[54] LARGE INTESTINAL DISSOCIATIVE HARD CAPSULES

[75] Inventors: Tsutomu Suzuki; Kenichi Hashiudo; Takayuki Matsumoto; Toshihiro Higashide, all of Toyohashi; Takeru Fujii, Naruto, all of Japan

[73] Assignee: Aicello Chemical Co., Ltd., Toyohashi, Japan

[21] Appl. No.: 709,978

[22] Filed: Jun. 4, 1991

[30] Foreign Application Priority Data

Jun. 4, 1990 [JP] Japan .................. 2-145678

[51] Int. Cl.$^5$ ................................ A61K 9/48
[52] U.S. Cl. ................................ 424/451; 424/436; 424/438; 424/459; 424/461; 424/463; 514/3; 514/808; 536/20
[58] Field of Search .............. 424/451, 459, 461, 463, 424/436, 438, 451; 514/808, 3; 536/20

[56] References Cited

U.S. PATENT DOCUMENTS

| | | | |
|---|---|---|---|
| 4,309,534 | 7/1982 | Austin | 536/20 |
| 4,670,287 | 6/1987 | Tsuji | 424/463 |
| 4,702,918 | 10/1987 | Ushimaru et al. | 424/461 |
| 4,808,707 | 2/1989 | Daly et al. | 424/461 |
| 4,814,176 | 3/1989 | Makino et al. | 424/457 |
| 4,895,724 | 1/1990 | Cardinal et al. | 424/461 |
| 4,910,021 | 3/1990 | Davis et al. | 424/463 |
| 5,089,272 | 2/1992 | Shioya et al. | 424/493 |

FOREIGN PATENT DOCUMENTS

| | | |
|---|---|---|
| 0173751 | 3/1986 | European Pat. Off. |
| 0454383 | 10/1991 | European Pat. Off. |
| 8901034 | 2/1989 | PCT Int'l Appl. |

*Primary Examiner*—Thurman K. Page
*Assistant Examiner*—Robert H. Harrison
*Attorney, Agent, or Firm*—Oblon, Spivak, McClelland, Maier & Neustadt

[57] ABSTRACT

A large intestinal dissociative hard capsule comprising a capsule mainly composed of chitosan, the viscosity at 20° C. of a solution obtained by dissolving the chitosan in an aqueous 1% by weight acetic acid solution being not higher than 100 cps and the degree of deacetilation of the chitosan being from 60 mol % to 98 mol %, having a coated layer of a polymer soluble in a liquid having pH of at least 5 on the surface of the capsule.

5 Claims, No Drawings

LARGE INTESTINAL DISSOCIATIVE HARD CAPSULES

FIELD OF THE INVENTION

The present invention relates to large intestinal dissociative (or disintegrating) hard capsules. More particularly, the invention relates to large intestinal dissociative capsules which are not dissociated in the digestive organs of from the oral cavity to the small intestine in the case of being orally administered and are first dissociated in the large intestine to release the medicament encapsulated therein.

BACKGROUND OF THE INVENTION

Hitherto, for facilitating taking medicines mainly having a strong bitterness and iritative property, gelatin hard capsules have been used. Also, these capsules are generally classified into ordinary gastric hard capsules which are dissolved in a stomach and entero soluble hard capsules which are not dissolved in a stomach but are dissociated in the small intestines. As the enteric capsules, there are known gelatin capsules, the surfaces of the capsules being coated with an alkali-soluble polymer and capsules using an alkali-soluble polymer itself as the base. These capsules utilize the difference in the solubility of the capsules by the difference in pH in the digestive organs. That is, these capsules are not dissolved in a strong acidic stomach having pH of from 1 to 3 but are dissolved in the weak alkaline small intestine such as the intestinum duodenum, the intestinum jejunum, and the intestinum ilium each having ph of from 7.5 to 9.3.

On the other hand, it has been clarified that peptide such as insulin and calcitonin, the absorption of which in digestive organs has been considered to be difficult, is very efficiently absorbed in the large intestine of the colon and the rectum. However, when a peptide preparation encapsulated in ordinary gelatin capsules is simply orally administered, the gelatin capsules are dissolved in a stomach to release the medicament, which is easily decomposed by gastric juices and intestinal protease such as pepsine, trypsin, etc., and loses its effect before reaching the large intestine. Also, even when the medicament is encapsulated in the entero soluble hard capsules as described above, these capsule medicine may pass through a stomach without being dissolved but are relatively easily dissolved in the intestinum duodenum and the small intestine, thereby the medicament is released, the decomposition thereof by intestinal protease can not be avoided, and the effective medical effect can not be expected.

Furthermore, there are similar problems in the medical treatment of a large intestine disease by the administration of medicine. For example, for the medical treatment for a ulcerative colitis, 5-aminosalicylic acid or prednisolone is used but when such an anti-inflammatory agent is orally administered in a state of being encapsulated in conventional capsules, the medicament is almost absorbed in the small intestine, thereby a large amount of administration is required for obtaining the medical effect and hence there is a large possibility of causing a side action.

For solving the foregoing problems, it has been desired to develop large intestinal dissociative capsules capable of making local administration of a medicament to the large intestine.

SUMMARY OF THE INVENTION

The object of this invention is, therefore, to provide large intestinal dissociative hard capsules capable of certainly transporting a medicament, which is chemically unstable and has a high absorbability in the large intestine, to the large intestine.

It has now been discovered that the foregoing object can be achieved by the present invention as described hereinbelow.

That is, according to this invention, there is provided large intestinal dissociative hard capsules comprising capsules mainly composed of chitosan, the viscosity at 20° C. of a solution formed by dissolving the chitosan in an aqueous 1% by weight acetic acid solution at a concentration of 1% by weight being not higher than 100 cps and the deacetylation degree of the chitosan being from 60 mol % to 98 mol %, having formed on the surface of the capsule a coated layer of a polymer soluble in a solution having pH of at least 5.

DETAILED DESCRIPTION OF THE INVENTION

As the result of various investigations for achieving the foregoing object, the inventors have discovered that capsules mainly composed of chitosan, the viscosity at 20° C. of a solution formed by dissolving the chitosan in an aqueous 1% by weight acetic acid solution at a concentration of 1% by weight being not higher than 100 cps and the deacetylation degree of the chitosan being from 60 mol % to 98 mol %, having formed on the surface of the capsule a coated layer of a polymer soluble in a solution having pH of at least 5 are most suitable as large intestinal dissociative hard capsules and have succeeded in accomplishing the present invention based on the discovery.

Chitosan is obtained by processing chitin largely contained in the outer shells of the Crustacea such as crabs, lobsters, etc., to completely or partially deacetylating the acetyl groups thereof but the chitosan being used in this invention is limited to the chitosan, the viscosity at 20° C. of a solution formed by dissolving the chitosan in an aqueous 1% by weight acetic acid solution at a concentration of 1% by weight being not higher than 100 cps, and preferably from 100 cps to 3 cps and the deacetylation degree of the chitosan being from 60 mol % to 98 mol %.

If chitosan, the viscosity of the solution of 1% by weight thereof being over 100 cps, is used, the concentration of a solution for forming capsules becomes very low and the formation of capsules becomes very difficult. For forming the capsules well, the concentration of chitosan in the solution is preferably at least 2% by weight, and more preferably at least 5% by weight. Also, if the degree of deacetylation of chitosan is less than 60 mol %, the solubility of chitosan in an acid solution is inferior, which results in reducing the forming property of capsules. Furthermore, in any cases, i.e., in the case that the viscosity of the solution of 1% by weight chitosan is over 100 cps or in the case that the degree of deacetylation of chitosan is less than 60 mol %, the solubility of the capsules in the pH range in the large intestine and the decomposability of the capsules by microorganisms and enzymes existing in the large intestine are poor, thereby the dissociation of the capsules for releasing a medicament contained therein can not be attained.

A polymer soluble in a solution having pH of at least 5, which is used for coating the surface of the capsules in this invention means a film-forming polymer which is sufficiently insoluble in a digestive fluid having pH of lower than 5, such as a gastric juice but is soluble in a digestive fluid having pH of 5 or higher and a polymer which is used for coating conventional enteric capsules or tablets can be used.

Examples of such a polymer are anionic acrylic resins such as a methacrylic acid-methyl methacrylate copolymer, a methacrylic acid-ethyl acrylate copolymer, etc., and anionic cellulose derivatives such as hydroxypropylmethyl cellulose acetate succinate, hydroxypropylmethyl cellulose phthalate, cellulose acetate phthalate, etc. In this invention, it is preferable to use the polymer as a solution thereof in an alcohol such as ethanol, isopropanol, etc., or a mixture of an alcohol and methylene chloride. Also, when fat and oil such as castor oil, etc., are added as a plasticizer at the preparation of the solution, an effect of preventing the cracking of the coated layers of the polymer is obtained.

For producing the large intestinal dissociative hard capsules of this invention, chitosan is first dissolved in an acid solution such as acetic acid, formic acid, etc. to form a chitosan solution, a rod-form mold having the capsule-form tip is immersed in the solution, the rod is pulled up at a constant speed, after drying by hot air, the capsule is drawn out from the mold, and cut into a desired size to form the capsule of chitosan. The chitosan capsule thus formed is not dissolved in the intestinum duodenum and the small intestine which are weak alkaline but it is preferred to increase the water resistance of the capsule by applying an alkali treatment for neutralizing a free acid by immersing the capsule after formed in an aqueous solution of an alkali such as sodium hydroxide, potassium hydroxide, sodium carbonate, etc., for a short time. The alkali treatment can be also carried out, after pulling out the mold from the chitosan solution in the foregoing capsule forming step, by immersing, in succession, the mold in an aqueous alkali solution and according to the method, the formation step of capsules can be shortened.

Also, if necessary, to the chitosan solution may be properly added a coloring agent, a light shielding agent, a spice, etc. Furthermore, for increasing the dissociative property of the capsules in the large intestine, a polysaccharide such as a cellulose and its derivatives powder, grain powder, starch powder, processed starch powder, oligosaccharide powder, etc., may be added to the chitosan solution and for increasing the rigidity of the capsules, an inorganic or organic filler can be mixed with the chitosan solution. In particular, in the case of adding a polysaccharide, it is preferred to add it in an amount of from 20 to 100% by weight to the chitosan to increase the dissociative property of the capsules.

The capsule is composed of a combination of, for example, a cylindrical body and cap having a different diameter and the spherical tip portion, and they are joined with each other.

To the surface of the capsule thus formed is applied coating of a polymer soluble in a solution having pH of at least 5 for imparting a gastric juice resistance to the capsule to complete the large intestinal dissociative hard capsule of this invention.

For applying gastric juice resisting coating to the capsule, a spray coater which is usually used for surface coating of preparations is most suitable but a dip coating method can be also employed. Gastric juice resisting coating may be applied to the aforesaid states of body and cap units but it is preferred to apply the coating after filling a medicament in the body unit and joining the body unit and the cap unit for completing the seal.

For filling a medicament such as insulin, etc., in the capsule of this invention, the medicament is dissolved in purified water, a physiological saline solution, or a buffer solution, after adding a binder such as lactose, hydroxypropyl cellulose, polyethylene glycol, various kinds of starches, etc., and further, if necessary, an absorption acceleration agent for a medicament from digestive organs and a stabilizer to the solution and after forming a solid agent such as fine grains, granules, etc., the solid agent of the medicament can be filled in the capsule.

The mechanism by which the hard capsule thus formed is dissociated in the large intestine has not yet been clarified but it is considered that chitosan is degraded or dissolved by an enzyme such as lysozyme, etc., or an acid metabolite produced from anaerobic microorganisms largely existing in the large intestine to dissociate the capsule.

By using the large intestinal dissociative hard capsules of this invention, peptide series medicaments such as insulin, carcitonine, etc., and anti-inflammatory agents such as 5-aminosalicylic acid, prednisolone, etc., which can hitherto be administered by injection only, can be orally administered, whereby not only the medial effect can be maintained long by the slow releasing property of the capsulated medicament but also the burden of patients by injection can be reduced, which makes the present invention very useful.

Then, the invention and the effect thereof are practically described by the following examples.

EXAMPLE 1

In 85 g of an aqueous 4% by weight acetic acid solution was dissolved 11 g of chitosan ("Flonac C-1" trade name, made by Kyowa Tecnos Co.) wherein the viscosity at 20° C. of the solution obtained by dissolving the chitosan in an aqueous 1% by weight acetic acid solution at a concentration of 1% by weight was 8 cps and the degree of deacetylation of the chitosan was 82 mol % to provide a base solution for forming capsules. A mold for a capsule was immersed in the base solution, after slowly pulling out the mold from the solution, the mold was immersed in an aqueous solution of 2% sodium hydroxide for one minute, and then dried by hot air at 70° C. for 20 minutes to form a chitosan capsule. The wall thickness of the capsule was about 70 $\mu$m in the whole range.

First, the dissociation test of the capsule with a large intestinal bacteria was practiced. As the test bacteria, *Bacteroides vulgatus* IFO 14291 which was the preferential bacteria in the large intestine was used. A red dye, Congo Red was filled in the above chitosan capsule, the joined portion of the body and the cap of the capsule was sealed with the chitosan solution used for the formation of the capsule, the capsule was then placed in a liquid prepared by suspending the foregoing bacterial in a physiological saline solution containing cysteine thioglycolate, and the system was shaked under an anaerobic condition for 9 hours at 37° C. As the result thereof, the dissolution of the dye in the suspension was observed after 3 hours and the dissociation of the capsule was confirmed after 6 hours.

Also, for comparison, the same test was performed in a physiological saline solution containing cysteine thioglycolate but not containing the foregoing bacteria, the dissolution of the dye and the dissociation of the capsule were not observed even after 9 hours, which showed clearly that the chitosan capsule was dissociated with the large intestinal bacteria.

Then, after filling a barium sulfate powder in the chitosan capsule, the capsule was sealed as described above and thereafter, the capsule was immersed in a solution obtained by dissolving 10 g of a methacrylic acidmethacrylmethyl copolymer ("Eudragit L, trade name, made by Röhm Phama Co.,) soluble at pH of at least 6 and 2 g of castor oil in 90 g of ethanol to form a gastric juice resisting coat of about 50 μm in thickness on the surface of the capsule. The capsule was orally administered in a stomach of beagle dogs and by taking X-ray photographs with the passage of time, the dissociated position of the capsule was inspected. As the result thereof, the capsule passed through the stomach and transferred to the upper part of the small intestine after 2 hours since the administration, and also the dissociation of the capsule was not observed until the capsule reached the large intestine after 4 to 6 hours. Also, after 10 hours since the administration, the images of barium sulfate dispersed, which confirmed that the capsule was dissociated.

EXAMPLE 2

To the aqueous acetic acid solution of chitosan ("Flonac C-1" trade name, made by Kyowa Tecnos Co.,) wherein the viscosity at 20° C. of the solution formed by dissolving the chitosan in an aqueous 1% by weight acetic acid solution at a concentration of 1% by weight was 8 cps and the degree of deacetylation of the chitosan was 82 mol % as in Example 1 was uniformly dispersed a powdery cellulose having a grain size of 400 mesh in the same amount as the chitosan to form a base solution and using the base solution, a capsule was formed by the same manner as in Example 1.

A barium sulfate powder was filled in the capsule followed by sealing with the base solution and gastric juice resisting coating was applied onto the surface of the capsule. These capsules were orally administered 6 fasted and feed beagle dogs (3 capsules for one dog) and by taking soft X-ray photographs with the passage of time, the dissociated positions of the capsules were inspected.

As the results, the time that the capsule reached the large intestine largely differs from 2 hours to 6 hours for each dog but in any cases, the capsules were not dissociated in the digestive organs before reaching the large intestine and all the capsules were dissociated in the large intestine.

EXAMPLE 3

A capsule having a composition composed of chitosan ("Flonac C-2" trade name, made by Kyowa Tecnos Co.,) wherein the viscosity at 20° C. of a solution obtained by dissolving the chitosan in an aqueous 1% by weight acetic acid solution at a concentration of 1% by weight was 33 cps and the degree of deacetylation of the chitosan was 76 mol % added with 70 parts by weight of rice starch to 100 parts by weight of the chitosan was formed according to the same manner as the formation method in Example 1. When the dissociation test of the capsule by the large intestinal bacterial was carried out as in Example 1, the dissolution of the dye was observed after 2 hours and after 6 hours, the dissociation of the capsule was confirmed.

Also, on the capsule having a gastric juice resisting coat applied on the surface thereof, when the dissociation position of the capsule was inspected using beagle dogs, the dissociation of the capsule was first observed in the large intestine after 7 hours since the administration.

EXAMPLE 4

In a mixed aqueous solution composed of 750 μl of an aqueous solution of 2% by weight polyoxyethylene (9)octylphenyl ether (Nonidet P-40, trade name, made by Sigma Co.), 150 μl of an aqueous solution of 1% by weight sodium caprate and 1500 μl of an aqueous solution of 0.3% by weight cattle serum albumin was dissolved 15 mg of human calcitonin to provide an aqueous calcitonine solution. Then, to the aqueous solution were added 0.5 g of lactose, 0.8 g of corn starch, 0.3 g of hydroxypropyl cellulose, and a small amount of a lead powder having a grain size of 200 mesh as a marker for soft X-ray perspective followed by sufficiently mixing to provide a base liquid for calcitonin preparations and after granulating the base liquid, the granules formed was vacuum-dried to provide granular calcitonin preparations having a diameter of 1 mm.

The calcitonin preparations thus obtained were filled in a capsule formed by the same manner as in Example 1 and the capsule was sealed and applied with a gastric juice resisting coating to provide a capsule preparation of calcitonin. The capsule was orally administered in a stomach of a beagle dog, by taking X-ray photographs with the passage of time, the dissociated position was inspected and also the calcitonin concentration of the serum was traced. In addition, the dosage of calcitonin was 360 μg.

As the result of the test, it was confirmed that the capsule was not dissociated in the digestive organs from the stomach to the small intestine and dissociated after reaching the large intestine after 4 to 6 hours since the administration. Also, the calcitonin concentration in the serum was shown in the following table. As shown in the table, the abrupt increase of the calcitonin concentration was observed corresponding to the dissociated time of the capsule.

TABLE

| Concentration change of calcitonin in serum | | | | | |
|---|---|---|---|---|---|
| Time after administration (hr.) | 0 | 2 | 4 | 6 | 8 | 10 |
| Calcitonin Concentration (pg/ml) | 51 | 44 | 70 | 286 | 180 | 47 |

COMPARISON EXAMPLE 1

For forming a capsule of chitosan ("Flonac N" trade name, made by Kyowa Tecnos Co.,) wherein the viscosity at 20° C. of a solution obtained by dissolving the chitosan in an aqueous 1% by weight acetic acid solution at a concentration of 1% by weight was 1500 cps and the degree of deacetylation of the chitosan was 85 mol %, when the chitosan was dissolved in an aqueous acetic acid solution, the highest concentration in the viscosity range capable of forming a capsule was 1.7% by weight When a capsule was formed using the above solution, by one step of the immersion of a mold, pulling up the mold, and drying, a capsule only having a very thin wall thickness was obtained and for obtaining a hard capsule capable of keeping the form, the foregoing step had to repeat several times, thereby the capsule formation efficiency was very low, and also the wall thickness of the capsule formed was not uniform.

When the dissociation test of the capsule by the large intestinal bacteria was performed as in Example 1, the dissolution of the dye and the dissociation of the capsule were not observed even after 9 hours and also in an oral administration test using beagle dogs, the dissociation of the capsule in the digestive organs was not observed.

COMPARISON EXAMPLE 2

By following the capsule forming method in Example 1 using chitosan ("Chitosan 10B" trade name, made by Katokichi Co.,) wherein the viscosity at 20° C. of a solution obtained by dissolving the chitosan in an aqueous 1% by weight acetic acid solution at a concentration of 1% by weight was 36 cps and the deacetylation degree of the chitosan was 99 mol %, a capsule was formed.

When the dissociation test of the capsule with the large intestinal bacteria was performed as in Example 1, the dissolution of the dye and the dissociation of the capsule were not observed even after 9 hours. Also, in an oral administration test using beagle dogs, the dissociation of the capsule in the digestive organs was not observed.

COMPARISON EXAMPLE 3

Barium sulfate was filled in a commercially available gelatin hard capsule, and after forming gastric juice resisting coating on the surface of the capsule as in Example 1, an oral administration test of the capsule was performed using beagle dogs. As the result, the capsule was not dissociated in the stomach but was dissociated in the intestinum duodenum after 5 hours since the administration.

What is claimed is:

1. A large intestinal dissociative hard capsule for oral administration comprising a capsule consisting essentially of chitosan, the viscosity at 20° C. of a solution obtained by dissolving the chitosan in an aqueous 1% by weight acetic acid solution at a concentration of 1% by weight being not higher than 100 cps and the degree of deacetylation of the chitosan being from 60 mol % to 98 mol %, having a coated layer of a polymer soluble in a liquid having pH of at least 5 on the surface of the capsule.

2. A large intestinal dissociative hard capsule for oral administration, wherein the capsule is composed of chitosan, the viscosity at 20° C. of a solution obtained by dissolving the chitosan in an aqueous 1% by weight acetic acid solution at a concentration of 1% by weight being no higher than 100 cps and the degree of deacetylation of the chitosan being from 60 mol % to 98 mol %, and a capsule dissociating agent, having a coated layer of a polymer soluble in a liquid having pH of at least 5 on the surface of the capsule.

3. The large intestinal dissociative hard capsule of claim 2, wherein the capsule dissociating agent is at least one kind of polysaccharide selected from a cellulose and its derivatives powder, a grain powder, starch powder, processed starch powder, and oligosaccharide powder.

4. The large intestinal dissociative capsule of any one of claims 1 to 3, wherein the polymer soluble in a liquid having pH of at least 5 is at least one kind of polymer selected from a methacrylic acid-methyl methacrylate copolymer, a methacrylic acid-ethyl acrylate copolymer, hydroxypropylmethyl cellulose acetate and succinate, and hydroxypropylmethyl cellulose phthalate.

5. The large intestinal dissociative hard capsule of any one of claims 1 to 3, wherein the surface of the capsule is subjected to an alkali treatment to increase its water resistance.

* * * * *